US00PP22342P2

(12) United States Plant Patent
Livingston

(10) Patent No.: US PP22,342 P2
(45) Date of Patent: Dec. 13, 2011

(54) ***HOSTA* PLANT NAMED 'ALAKAZAAM'**

(50) Latin Name: ***Hosta* hybrid**
Varietal Denomination: Alakazaam

(76) Inventor: Ronald A. Livingston, Clawson, MI (US)

( * ) Notice: Subject to any disclaimer, the term of this patent is extended or adjusted under 35 U.S.C. 154(b) by 0 days.

(21) Appl. No.: 12/803,651

(22) Filed: Jul. 1, 2010

(51) Int. Cl.
*A01H 5/00* (2006.01)

(52) U.S. Cl. ..... Plt./353

(58) Field of Classification Search ..... Plt./353
See application file for complete search history.

*Primary Examiner* — Annette Para

(57) ABSTRACT

A new and distinct *Hosta* plant named 'Alakazaam' characterized by compact short habit with predominantly horizontal lance-shaped leaves of, apple-green with rippled pie-crust margins of yellow to creamy white and lavender flowers beginning in mid July, effective for three weeks.

1 Drawing Sheet

Botanical classification: *Hosta* hybrid (Tratt.)
Variety denomination: 'Alakazaam'

BACKGROUND AND ORIGIN OF THE PLANT

The present invention relates to the new and distinct *hosta* plant, *Hosta* 'Alakazaam' hybridized by Ronald Livingston in the summer of 2000 at a garden in Clawson, Mich. and was separated as a seedling of potential in May 2002. The new plant is the result of a controlled cross between the proprietary seedling 'M12A' (not patented) as the female or pod parent and *Hosta* 'Atom Smasher' (not patented) as the male or pollen parent. *Hosta* 'Alakazaam' has been asexually propagated by division at the same garden in Clawson, Mich. in 2006 and all resulting plants have retained all the same traits as the original plant. The plant has also been propagated by tissue culture at a nursery in Zeeland, Mich., with the resultant plants of this asexual propagation maintaining all the same traits as the original plant. The plant is stable and reproduces true to type in successive generations of asexual reproduction.

The most similar known *hosta* cultivars known to the applicant are: *Hosta* 'Pineapple Punch' U.S. Plant Pat. No. 18,318 and 'Atom Smasher' (not patented). 'Pineapple Punch' has a much larger leaf and habit, a darker leaf center and taller flower scapes than 'Alakazaam'. 'Atom Smasher', the pollen parent, has solid yellow leaves and smaller habit than 'Alakazaam'.

*Hosta* 'Alakazaam' differs from all other *hostas* known to the applicant, by the combination of the following traits.

1. Compact short habit with predominantly horizontal leaves.
2. Lance-shaped apple-green leaves with rippled pie-crust margin of yellow to creamy white.
3. Lavender flowers beginning in mid July.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, temperature, source and direction may cause the appearance of minor variation in color.

DETAILED BOTANICAL DESCRIPTION

Figure 1:
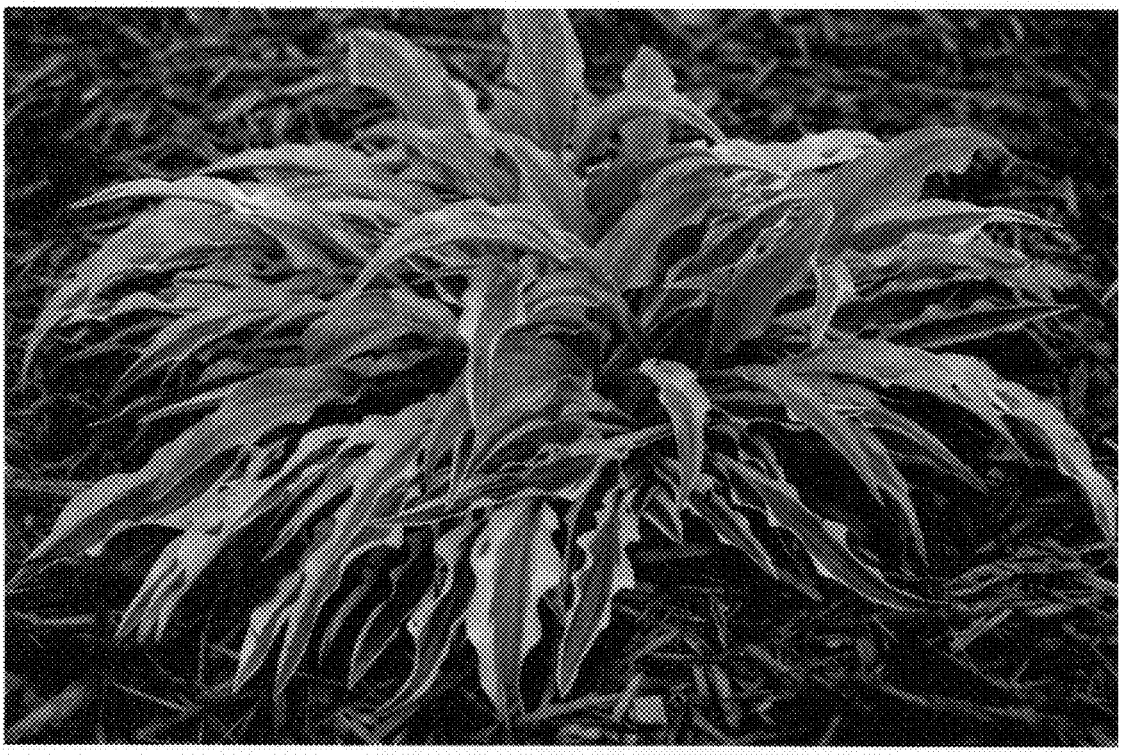
FIG. 1 shows the new plant in the landscape.
Figure 2:
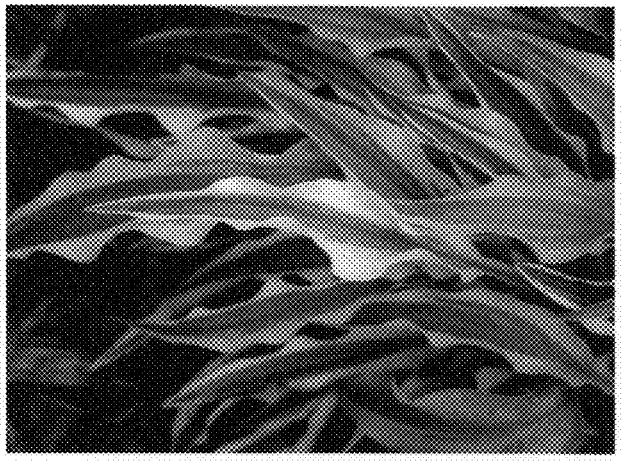
FIG. 2 shows a close-up of the leaves of the new plant.

The following descriptions and color references are based on the 2001 edition of The Royal Horticultural Society Colour Chart except where common dictionary terms are used. The new plant, *Hosta* 'Alakazaam', has not been observed under all possible environments. The phenotype may vary slightly with different environmental conditions, such as temperature, light, fertility, moisture and maturity levels, but without any change in the genotype. The following observations and size descriptions are of a three-year old plant in a 50% shaded trial garden in Zeeland, Mich. with and supplemental water and fertilizer.

Botanical classification: *Hosta* hybrid;
Parentage:
*Female.*—Proprietary seedling 'M12A' (not patented).
*Male.*—'Atom Smasher'.
Propagation: Garden division and sterile plant tissue culture;
Time to initiate roots from tissue culture: About two and a half weeks;
Growth rate: Moderate;
Crop time: About 14 to 18 weeks to finish during the summer in a one-liter container from rooted tissue culture plantlet;
Rooting habit: Fleshy, lightly branching, with roots up to 25 cm long;
Plant shape and habit: Hardy herbaceous perennial with basal rosette of leaves emerging from rhizomes producing a symmetrical mound of very horizontal leaves in youth, becoming slightly more upright with age;
Plant size: Foliage height about 17 cm tall from soil line to the top of the leaves and about 45 cm wide at the widest point just above soil line;
Foliage description: Lanceolate rounded, acute leaf apex with attenuate base; rippled or piecrust undulation along margin; up to 22 cm long and 4.5 cm wide, average 18 cm long and 2.7 cm wide;

Leaf blades: Simple, entire, with undulated margin; slightly folded up along mid-rib length of leaf; bilaterally symmetrical; glabrous and dull surface on top, glabrous and shiny below, variegation pattern variable with the margin between about 0.5 cm to 1.0 cm wide with some jetting of margin or center color into the edge or center;

Leaf blade color: Emerging adaxial (top) margin color between RHS 151B and RHS 151C; emerging abaxial (underside) margin nearest RHS 151D; emerging center adaxial between RHS 144A and RHS 144B; emerging abaxial center nearest RHS 1444B; older leaves later in summer adaxial margins RHS 11D; older abaxial margins RHS 11D; older adaxial center nearest RHS 143A and abaxial center nearest RHS 143A;

Petiole: Entire, glabrous; mostly straight from base of plant to leaf base, concave center, slightly stiff; up to 9.0 cm long and about 0.7 cm wide at base, average about 4.5 cm long and 0.6 cm wide;

Petiole color: Identical to leaf blades and changing with age as in the blade;

Veins: Parallel, slightly raised on abaxial side, 4 to 5 pair;

Veins color: Same as surrounding leaf on both adaxial and adaxial sides and transition as leaf color through the season;

Flower description:

Buds one day prior to opening: About 1.2 cm diameter at widest point and 5.0 cm long; globose apex with base narrowing to a diameter of about 4 mm in diameter; lavender between RHS N82B and RHS N82C in the distal ⅔s of the bud with the proximal ⅓ nearest RHS 76D with green tinting lighter than RHS 138D;

Flowers: Funnelform; with broadly flared tepals; 20 to 25 per scape; 3.8 to 4.5 cm wide and 5.0 to 6.5 cm long, (distal flowers smaller), persists for a normal period, usually one day on plant or as cut flower; scapes remain effective with flowers from mid-July to early-August; no detectable fragrance;

Bracts: Each flower subtended by a single bract to 1.5 cm long and 7.0 mm wide decreasing in size distally; glaucous and glabrous both surfaces, margin entire, sessile with straight base, apex acute; concaved supporting flower bud; abaxial color nearest RHS 139B with a 1.0 mm wide margin of nearest RHS 145C; adaxial color nearest RHS 144A with a 1.0 mm wide margin of nearest RHS 145B; color persists beyond flower senescence;

Tepal: Two sets of three, fused at base; clavate with obtuse to cuspidate apex; glabrous, entire; approximately 3.0 cm long and 1.5 cm wide; coloring of both sets identical except outer set of three tepals with a 1.0 mm wide white margin; medium lavender; abaxial tepal surface nearest RHS 85D in distal ⅔'s and much whiter than RHS 85D in proximal third with the basal 2 to 3 mm darkening to nearest RHS N87C; adaxial tepals surface nearest RHS N87D darkening near center to nearest RHS N87C with the basal tube white, three veins nearest RHS 83B running from almost the tepal apex to within one third of the way to the base;

Gynoecium: Style: single, 3.5 to 4.0 cm long, 1 mm diameter, curled upward at distal end; color closer to white than RHS 145D;

*Stigma.*—Globose, about 1 mm in diameter, near white; nearest RHS 155C.

Androecium: Filaments: six, white, whiter than RHS 155D, less than 1 mm in diameter and 3.0 cm long;

*Anthers.*—2 to 3 mm long, 1 mm wide, dehiscent longitudinally; nearest RHS 158A;

*Pollen.*—Elliptical, less than 0.1 mm long, nearest RHS 17A.

Peduncle: One per mature division; glaucous; glabrous; without vertical ridges; 80 to 90 degrees from horizontal; to 54 cm tall, and up to 5 mm in diameter at base; nearest RHS 146C;

Pedicel: Approximately 8 mm long, 2 mm wide; RHS 138 C;

Fruit: Tri-loculicidal capsule, about 2.5 to 3.0 cm long and 7 mm diameter; nearest RHS 144A with tinting nearest RHS 186D while maturing to nearest RHN 165C;

Seed: Flattened single-winged nutlet with swollen embryo at one end; about 8 mm long, 2 mm wide and 1 mm thick at embryo; nearest RHS 202A;

Disease resistance: Resistance to pests and diseases beyond that of other *hosta* has not been observed. The plant grows best and shows best coloration with plenty of moisture, adequate drainage and light shade, but is able to tolerate some drought when mature. Hardiness at least from USDA zone 3 through 9, and other disease resistance is typical of that of other *hostas.*

I claim:

1. A new and distinct cultivar of ornamental *Hosta* plant named 'Alakazaam' as herein described and illustrated, with compact short habit with predominantly horizontal leaves of apple green with rippled pie-crust margin of yellow to creamy white and lavender flowers beginning in mid July, suitable as a potted plant, for the garden, and for cut flower arrangements.

* * * * *